(12) United States Patent
Weitzman

(10) Patent No.: US 11,564,915 B2
(45) Date of Patent: Jan. 31, 2023

(54) CABOZANTINIB DOSAGE FORM AND USE IN THE TREATMENT OF CANCER

(71) Applicant: Exelixis, Inc., Alameda, CA (US)

(72) Inventor: Aaron Weitzman, Menlo Park, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 14/782,537

(22) PCT Filed: Apr. 4, 2014

(86) PCT No.: PCT/US2014/033016
§ 371 (c)(1),
(2) Date: Oct. 5, 2015

(87) PCT Pub. No.: WO2014/165786
PCT Pub. Date: Oct. 9, 2014

(65) Prior Publication Data
US 2016/0022662 A1    Jan. 28, 2016

Related U.S. Application Data

(60) Provisional application No. 61/808,511, filed on Apr. 4, 2013.

(51) Int. Cl.
| | | |
|---|---|---|
| *A61K 31/47* | (2006.01) | |
| *A61K 9/20* | (2006.01) | |
| *A61K 9/00* | (2006.01) | |
| *A61K 9/28* | (2006.01) | |
| *A61K 31/194* | (2006.01) | |

(52) U.S. Cl.
CPC ........... *A61K 31/47* (2013.01); *A61K 9/0053* (2013.01); *A61K 9/2054* (2013.01); *A61K 9/282* (2013.01); *A61K 9/2813* (2013.01); *A61K 9/2866* (2013.01); *A61K 31/194* (2013.01)

(58) Field of Classification Search
CPC .... A61K 9/2054; A61K 31/47; A61K 9/0053; A61K 31/194; A61K 9/282; A61K 9/2866; A61K 9/2813
See application file for complete search history.

(56) References Cited

U.S. PATENT DOCUMENTS

| | | | |
|---|---|---|---|
| 7,579,473 | B2 | 8/2009 | Bannen et al. |
| 7,977,345 | B2 | 7/2011 | Bannen et al. |
| 7,999,006 | B2 | 8/2011 | Lamb |
| 8,067,436 | B2 | 11/2011 | Bannen et al. |
| 8,178,532 | B2 | 5/2012 | Bannen et al. |
| 8,314,232 | B2 | 11/2012 | Deschamps et al. |
| 8,476,298 | B2 | 7/2013 | Bannen et al. |
| 8,497,284 | B2 | 7/2013 | Bannen et al. |
| 8,673,912 | B2 | 3/2014 | Cannon et al. |
| 8,877,776 | B2 | 11/2014 | Brown et al. |
| 9,174,947 | B2 | 11/2015 | Bannen et al. |
| 9,365,516 | B2 | 6/2016 | Wilson et al. |
| 9,717,720 | B2 | 8/2017 | Wilson et al. |
| 9,724,342 | B2 | 8/2017 | Wilson et al. |
| 9,809,549 | B2 | 11/2017 | Brown et al. |
| 9,861,624 | B2 | 1/2018 | Aftab et al. |
| 9,969,692 | B2 | 5/2018 | Wilson et al. |
| 10,034,873 | B2 | 7/2018 | Wilson et al. |
| 10,039,757 | B2 | 9/2018 | Wilson et al. |
| 10,159,666 | B2 | 12/2018 | Aftab et al. |
| 10,166,225 | B2 | 1/2019 | Aftab et al. |
| 10,273,211 | B2 | 4/2019 | Aftab et al. |
| 2007/0066610 | A1* | 3/2007 | Leonard ................. A61P 35/00 514/233.5 |
| 2008/0161305 | A1 | 7/2008 | Forsyth et al. |
| 2009/0068179 | A1* | 3/2009 | Nayeri ............... C07K 16/2863 424/133.1 |
| 2009/0274693 | A1 | 11/2009 | Gilmer et al. |
| 2011/0077233 | A1 | 3/2011 | Bannen et al. |
| 2011/0293726 | A1* | 12/2011 | de los Rios ............... A61P 9/10 424/490 |
| 2012/0070368 | A1 | 3/2012 | Bannen et al. |
| 2012/0184523 | A1 | 7/2012 | Bannen et al. |
| 2012/0252840 | A1 | 10/2012 | Aftab et al. |
| 2012/0282179 | A1 | 11/2012 | Aftab et al. |
| 2013/0030172 | A1 | 1/2013 | Wilson et al. |
| 2013/0142790 | A1 | 6/2013 | Gilmer et al. |
| 2013/0143881 | A1 | 6/2013 | Cannon et al. |
| 2013/0150363 | A1 | 6/2013 | Gilmer et al. |
| 2013/0197230 | A1 | 8/2013 | Wilson et al. |
| 2013/0252940 | A1 | 9/2013 | Bannen et al. |
| 2013/0252956 | A1 | 9/2013 | Kallender et al. |
| 2013/0330377 | A1 | 12/2013 | Wilson |
| 2013/0337015 | A1 | 12/2013 | Wilson et al. |

(Continued)

FOREIGN PATENT DOCUMENTS

| | | | |
|---|---|---|---|
| WO | WO 2010/003992 | * | 1/2010 |
| WO | WO 2010/083414 | * | 7/2010 |

(Continued)

OTHER PUBLICATIONS

International Search Report for PCT/US2014/033016, dated Jul. 10, 2014.
Ciccarese, et al., "Exceptional Response to Cabozantinib of Rapidly Evolving Brain Metastases of Renal Cell Carcinoma: A Case Report and Review of the Literature", Clinical Genitourinary Cancer, vol. 16, No. 5, pp. 1069-1071, Jun. 21, 2018.
Drilon, A., et al., "Baseline frequency of brain metastases and outcomes with multikinase inhibitor therapy in patients with RET-rearranged lung cancers", Journal of Clinical Oncology, vol. 35, No. 15, suppl, pp. 9069-9069, May 20, 2017.
Ratta, et al., "Bone Metastases in Metastatic Renal Cell Carcinoma: Now We Know That Cabozantinib Targets Bone Microenvironment," Jounrla of Clinical & Experimental Nephrology, vol. 3, No. 1:03, Feb. 16, 2018.

(Continued)

Primary Examiner — Genevieve S Alley
(74) Attorney, Agent, or Firm — Honigman LLP; Heidi M. Berven

(57) ABSTRACT

This invention relates to a dosage form of cabozantinib and a method of employing the dosage form to treat cancer.

3 Claims, No Drawings

(56) References Cited

U.S. PATENT DOCUMENTS

| | | | |
|---|---|---|---|
| 2014/0057908 A1 | 2/2014 | Smith et al. | |
| 2014/0057943 A1 | 2/2014 | Smith et al. | |
| 2014/0066444 A1 | 3/2014 | Smith et al. | |
| 2014/0086926 A1* | 3/2014 | Jeong | C07K 16/2863 424/139.1 |
| 2014/0121239 A1 | 5/2014 | Aftab | |
| 2014/0155396 A1 | 6/2014 | Bannen et al. | |
| 2014/0179736 A1 | 6/2014 | Schwab et al. | |
| 2014/0200242 A1 | 7/2014 | Wilson | |
| 2014/0221372 A1 | 8/2014 | Kulkarni et al. | |
| 2014/0228401 A1 | 8/2014 | Aftab et al. | |
| 2014/0302012 A1 | 10/2014 | Aftab et al. | |
| 2014/0323522 A1 | 10/2014 | Aftab et al. | |
| 2015/0057310 A1 | 2/2015 | Brown et al. | |
| 2015/0133494 A1 | 5/2015 | Aftab et al. | |
| 2015/0196545 A1 | 7/2015 | Aftab et al. | |
| 2015/0202196 A1 | 7/2015 | Bannen et al. | |
| 2015/0238477 A1 | 8/2015 | Aftab | |
| 2015/0376133 A1 | 12/2015 | Bannen et al. | |
| 2016/0000772 A1 | 1/2016 | Aftab et al. | |
| 2016/0022662 A1 | 1/2016 | Decillis et al. | |
| 2016/0031818 A1 | 2/2016 | Aftab et al. | |
| 2016/0051532 A1 | 2/2016 | Aftab et al. | |
| 2016/0082019 A1 | 3/2016 | Sweeney et al. | |
| 2016/0185725 A1 | 6/2016 | Bannen et al. | |
| 2016/0220554 A1 | 8/2016 | Smith et al. | |
| 2016/0229805 A1 | 8/2016 | Wilson et al. | |
| 2017/0044106 A1 | 2/2017 | Aftab et al. | |
| 2017/0057921 A1 | 3/2017 | Wilson et al. | |
| 2017/0143689 A1 | 5/2017 | Wilson et al. | |
| 2017/0266178 A1 | 9/2017 | Wilson et al. | |
| 2017/0275251 A1 | 9/2017 | Brown et al. | |
| 2017/0355678 A1 | 12/2017 | Bannen et al. | |
| 2018/0002289 A1 | 1/2018 | Brown et al. | |
| 2018/0037552 A1 | 2/2018 | Brown et al. | |
| 2018/0230100 A1 | 8/2018 | Wilson et al. | |
| 2018/0311229 A1 | 11/2018 | Wilson et al. | |
| 2019/0030021 A1 | 1/2019 | Wilson et al. | |
| 2019/0076420 A1 | 3/2019 | Aftab et al. | |
| 2019/0091215 A1 | 3/2019 | Aftab et al. | |
| 2019/0151302 A1 | 5/2019 | Aftab et al. | |
| 2019/0218182 A1 | 7/2019 | Aftab et al. | |

FOREIGN PATENT DOCUMENTS

| | | | |
|---|---|---|---|
| WO | WO 2012/009723 | * | 1/2012 |
| WO | 2013166296 | | 11/2013 |
| WO | 2014039971 | | 3/2014 |

OTHER PUBLICATIONS

Santini, et al., "Natural History of Malignant Bone Disease in Renal Cancer: Final Results of an Italian Bone Metastasis Survey", PLoS One 8(12): e83026. https://doi.org/10.1371/journal.pone.0083026. Dec. 30, 2013.

Cerami, Ethan, et al., "The eBio Cancer Genomics Portal: An Open Platform for Exploring Multidimensional Cancer Genomics Data" Cancer Discov., 2(5): 401-404; May 2012; https://www.ncbi.nlm.nih.gov/pmc/articles/PMC3956037/.

Bagley et al. Endothelial Precursor Cells as a Model of Tumor Endothelium: Characterization and Comparison with Mature Endothelial Cells. Cancer Research 63 5866-5873 (2003), p. 5873, left column, Available at https://web.archive.org/web/20200710195135id_/https://cancerres.aacrjournals.org/content/canres/63/18/5866.full.pdf.

Okuda et al. "Genetics of Endometrial Cancers", Obstetrics and Gynecology International, vol. 2010, Article ID 984013, 8 pages, 2010. https://doi.org/10.1155/2010/984013.

Wang et al. "Genomic Characterization of Gene Copy-Number Aberrations in Endometrial Carcinoma Cell Lines Derived from Endometrioid-Type Endometrial Adenocarcinoma", Technology in Cancer Research and Treatment, vol. 9, No. 2, Apr. 2010, ISSN 1533-0346.

Konopka et al. PIK3CA mutations and amplification in endometrioid endometrial carcinomas: relation to other genetic defects and clinicopathologic status of the tumors, Human Pathology, vol. 42, Issue 11, 2011, pp. 1710-1719, ISSN 0046-8177, https://doi.org/10.1016/j.humpath.2010.01.030. (https://www.sciencedirect.com/science/article/pii/S0046817711000542).

Banno et al. "Biomarkers in endometrial cancer: Possible clinical applications (Review)". Oncology Letters 3.6 (2012): 1175-1180.

Levine et al. Cancer Genome Atlas Research Network, Integrated genomic characterization of endometrial carcinoma. Nature. May 2, 2013;497(7447):67-73. doi: 10.1038/nature12113. Erratum in: Nature. Aug. 8, 2013;500 (7461):242. PMID: 23636398; PMCID: PMC3704730.

Jardim et al. "Analysis of 1,115 Patients Tested for MET Amplification and Therapy Response in the MD Anderson Phase I Clinic" Clin Cancer Res; 20(24) Dec. 15, 2014, 6336-6345.

He et al. "Expression and correlation of C-met and estrogen receptor in endometrial carcinomas". Sichuan Da Xue Xue Bao Yi Xue Ban. Jan. 2003;34(1):78-9, 88. Chinese. PMID: 15600187.

Dhani et al. "Phase II Trial of Cabozantinib in Recurrent/Metastatic Endometrial Cancer: A Study of the Princess Margaret, Chicago, and California Consortia (NCI9322/PHL86)". Clin Cancer Res. Jun. 1, 2020;26(11):2477-2486. doi 10.1158/1078-0432.CCR-19-2576. Epub Jan. 28, 2020. PMID: 31992589; PMCID: PMC7269808.

* cited by examiner

CABOZANTINIB DOSAGE FORM AND USE IN THE TREATMENT OF CANCER

CROSS-REFERENCE TO RELATED APPLICATIONS

This application is a United States National Phase filing of PCT/US2014/033016, filed Apr. 4, 2014, which claims the benefit of U.S. Provisional Application No. 61/808,511, filed Apr. 4, 2013, the entire contents of which are incorporated herein by reference.

FIELD OF INVENTION

This invention relates to a dosage form of cabozantinib and a method of employing the dosage form to treat cancer.

BACKGROUND OF THE INVENTION

Traditionally, dramatic improvements in the treatment of cancer are associated with identification of therapeutic agents acting through novel mechanisms. One mechanism that can be exploited in cancer treatment is the modulation of protein kinase activity because signal transduction through protein kinase activation is responsible for many of the characteristics of tumor cells. Protein kinase signal transduction is of particular relevance in, for example, thyroid, gastric, head and neck, lung, breast, prostate, and colorectal cancers, as well as in the growth and proliferation of brain tumor cells. Protein kinases can be categorized as receptor type or non-receptor type. Receptor-type tyrosine kinases are comprised of a large number of transmembrane receptors with diverse biological activity. For a detailed discussion of the receptor-type tyrosine kinases, see Plowman et al., DN&P 7(6): 334-339, 1994. Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases, including, for example, immunological disorders, cardiovascular diseases, inflammatory diseases, and degenerative diseases. Therefore, protein kinases are attractive targets for small molecule drug discovery. Particularly attractive targets for small-molecule modulation with respect to antiangiogenic and antiproliferative activity include receptor type tyrosine kinases Ret, c-Met, and VEGFR2.

The kinase c-Met is the prototypic member of a subfamily of heterodimeric receptor tyrosine kinases (RTKs) which include Met, Ron, and Sea. The endogenous ligand for c-Met is the hepatocyte growth factor (HGF), a potent inducer of angiogenesis. Binding of HGF to c-Met induces activation of the receptor via autophosphorylation resulting in an increase of receptor dependent signaling, which promotes cell growth and invasion. Anti-HGF antibodies or HGF antagonists have been shown to inhibit tumor metastasis in vivo (See Maulik et al, Cytokine & Growth Factor Reviews, 2002, 13, 41-59). c-Met, VEGFR2, and/or Ret overexpression has been demonstrated on a wide variety of tumor types, including breast, colon, renal, lung, squamous cell myeloid leukemia, hemangiomas, melanomas, and astrocytic tumor (which includes glioblastoma, giant cell glioblastoma, gliosarcoma, and glioblastoma with oligodendroglial components). The Ret protein is a transmembrane receptor with tyrosine kinase activity. Ret is mutated in most familial forms of medullary thyroid cancer. These mutations activate the kinase function of Ret and convert it into an oncogenic form.

Accordingly, small-molecule compounds that specifically inhibit, regulate, and/or modulate the signal transduction of kinases, particularly including Ret, c-Met, and VEGFR2 described above, are particularly desirable as a means to treat or prevent disease states associated with abnormal cell proliferation and angiogenesis. One such small-molecule is XL184, known variously as N-(4-{[6,7-bis(methyloxy)quinolin-4-yl]oxy}phenyl)-N'-(4-fluorophenyl)cyclopropane-1,1-dicarboxamide and by the name cabozantinib (COMETRIQ™). Cabozantinib (Compound 1) has the chemical structure:

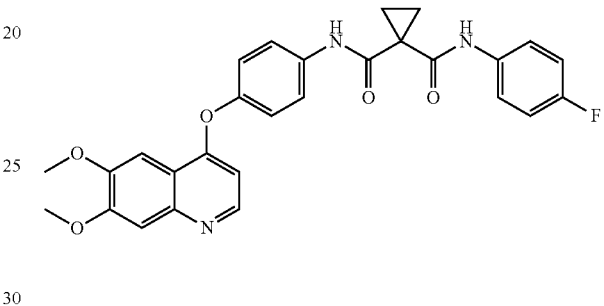

In November, 2012, cabozantinib achieved regulatory approval in the United States for the treatment of progressive metastatic medullary thyroid cancer. Other clinical trials of cabozantinib are ongoing.

A need remains for identifying optimal dosages of cabozantinib to treat cancer.

SUMMARY OF THE INVENTION

These and other needs are met by the present invention which is directed a pharmaceutical dosage comprising 60 mg of compound 1:

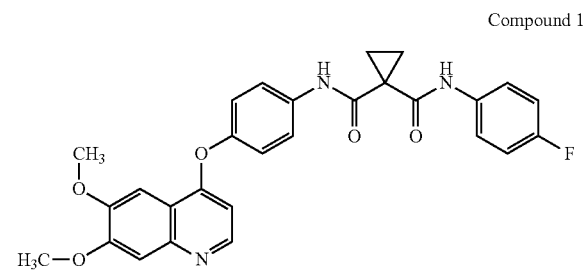 [SMILES: COc1cc2nccc(Oc3ccc(NC(=O)C4(C(=O)Nc5ccc(F)cc5)CC4)cc3)c2cc1OC]

Compound 1 or a pharmaceutically acceptable salt thereof or a pharmaceutical composition comprising compound 1 and a pharmaceutically acceptable carrier.

In one aspect, the pharmaceutical dosage comprising 60 mg of compound 1 is administered to a patient that had one or more adverse event at a dosage greater than 60 mg of compound 1.

Another aspect is a pharmaceutical dosage comprising 40 mg of compound 1:

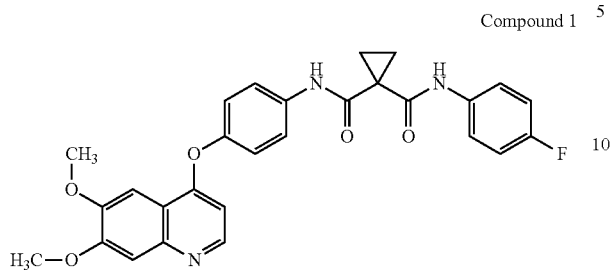
Compound 1 or a pharmaceutically acceptable salt thereof or a pharmaceutical composition comprising compound 1 and a pharmaceutically acceptable carrier.

In one aspect, the pharmaceutical dosage comprising 40 mg of compound 1 is administered to a patient that had one or more adverse event at a dosage greater than 40 mg of compound 1.

Another aspect is a pharmaceutical dosage comprising 20 mg of compound 1:

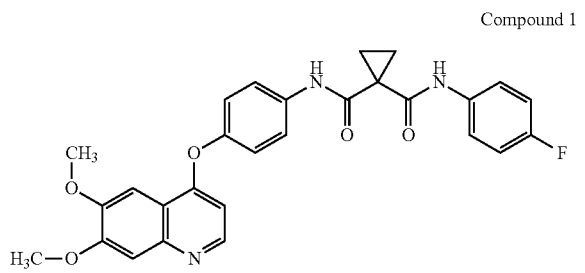 [SMILES: COc1cc2nccc(Oc3ccc(NC(=O)C4(C(=O)Nc5ccc(F)cc5)CC4)cc3)c2cc1OC]
Compound 1 or a pharmaceutically acceptable salt thereof or a pharmaceutical composition comprising compound 1 and a pharmaceutically acceptable carrier.

In one aspect, the pharmaceutical dosage comprising 20 mg of compound 1 is administered to a patient that had one or more adverse event at a dosage greater than 20 mg of compound 1.

Cabozantinib is formulated as the S-malate salt of N-(4-{[6,7-bis(methyloxy)quinolin-4-yl]oxy}phenyl)-N'-(4-fluorophenyl)cyclopropane-1,1-dicarboxamide, the structure of which is depicted below.

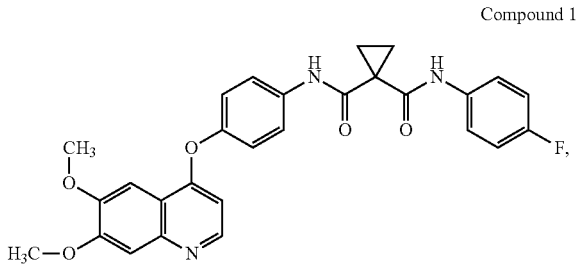
Compound 1

-continued

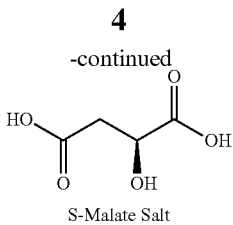
S-Malate Salt

WO 2005/030140, the entire contents of which is incorporated herein by reference, discloses compound 1 and describes how it is made and also discloses the therapeutic activity of this compound to inhibit, regulate, and/or modulate the signal transduction of kinases (Assays, Table 4, entry 289). WO 2005/030140 describes the synthesis of cabozantinib (Example 48) and also discloses the therapeutic activity of this molecule to inhibit, regulate, and/or modulate the signal transduction of kinases, (Assays, Table 4, entry 289). Example 48 is on paragraph [0353] in WO 2005/030140.

In another aspect, the invention is directed to methods of using the dosage forms to treat a variety of cancers.

DETAILED DESCRIPTION

Definitions

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to:
Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Breast; Colon; and Adrenal glands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

"Adverse event," or "AE," as used herein, means any undesirable experience associated with the use of a medical product in a patient. Examples of adverse events include diarrhea, stomatitis, palmar-plantar erythrodysesthesia syndrome (PPES), decreased weight, decreased appetite, nausea, fatigue, oral pain, hair color changes, dysgeusia, hypertension, abdominal pain, constipation, increased AST, increased ALT, lymphopenia, increased alkaline phosphatase, hypocalcemia, neutropenia, thrombocytopenia, hypophosphatemia, hyperbilirubinemia, perforations, fistulas, hemorrhage, thromboembolic events, wound complications, osteonecrosis of the jaw, proteinuria, reversible posterior leukoencephalopathy syndrome (RPLS), and embryofetal toxicity.

Adverse events are graded 1-5. A Grade 1 adverse event is mild, with no or mild symptoms and requires no interventions. Examples include mild fatigue that is relieved by rest, a low-grade fever, and asymptomatic or mild infections. A Grade 2 adverse event is moderate and requires minimal intervention and some limitation of activities. Examples include fatigue that is not relieved by rest, fever, and amnesia. A Grade 3 adverse event is severe but not life-threatening and may require hospitalization. It limits a patient's ability to care for him- or herself. Examples include hepatic failure, severe infections, and febrile neutropenia. A Grade 4 adverse event is life-threatening and requires urgent intervention. Examples include high fever lasting more than 24 hours and severe infections requiring intervention. A Grade 5 adverse event is characterized as death related to an adverse event. For more information on grading of adverse events, see *Common Terminology Criteria for Adverse Events*, US Department of Health and Human Services, National Institutes of Health, National Cancer Institute, Version 4.03, published Jun. 14, 2010.

Embodiments

In one aspect, the invention is directed to a pharmaceutical dosage comprising 60 mg of compound 1:

Compound 1

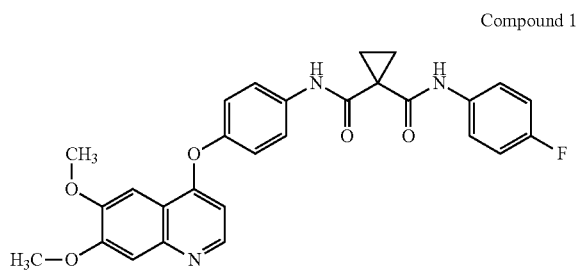 [SMILES: COc1cc2nccc(Oc3ccc(NC(=O)C4(C(=O)Nc5ccc(F)cc5)CC4)cc3)c2cc1OC]

or a pharmaceutically acceptable salt thereof or a pharmaceutical composition comprising compound 1 and a pharmaceutically acceptable carrier.

In one aspect, the invention is directed to a pharmaceutical dosage comprising 40 mg of compound 1:

Compound 1

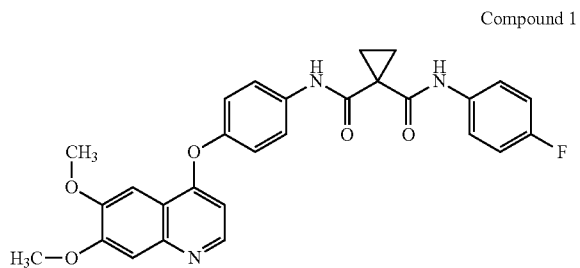 [SMILES: COc1cc2nccc(Oc3ccc(NC(=O)C4(C(=O)Nc5ccc(F)cc5)CC4)cc3)c2cc1OC]

or a pharmaceutically acceptable salt thereof or a pharmaceutical composition comprising compound 1 and a pharmaceutically acceptable carrier.

In one aspect, the invention is directed to a pharmaceutical dosage comprising 20 mg of compound 1:

Compound 1

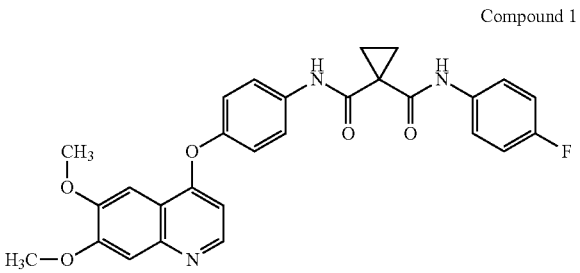

or a pharmaceutically acceptable salt thereof or a pharmaceutical composition comprising compound 1 and a pharmaceutically acceptable carrier.

In one embodiment of each aspect, compound 1 can be the (S)-malate salt. The malate salt of the compound of formula I and of compound 1 is disclosed in PCT/US2010/021194 and U.S. Patent Application Ser. No. 61/325,095, the entire contents of each of which are incorporated herein by reference.

In other embodiments, compound 1 can be the malate salt.

In other embodiments, compound 1 can be (R)-malate salt.

In other embodiments, compound 1 can be the (S)-malate salt.

In another embodiment, the malate salt is in the crystalline N-1 form of the (S) malate salt and/or the (R) malate salt of the compound 1 as disclosed in U.S. Patent Application Ser. No. 61/325,095. Also see WO 2008/083319 for the properties of crystalline enantiomers, including the N-1 and/or the N-2 crystalline forms of the malate salt of compound 1, which is incorporated herein by reference in its entirety. Methods of making and characterizing such forms are fully described in PCT/US10/21194, which is incorporated herein by reference in its entirety.

In one embodiment, compound 1 is administered as a tablet or capsule containing compound 1 as the S-malate salt and pharmaceutically acceptable carriers and excipients. In some embodiments, compound 1 is administered as a tablet. In other embodiments, compound 1 is administered as a capsule.

The desired dosage of compound 1 can be achieved using a combination of tablets or capsules as needed. For example to achieve a target dose of 20 mg would require administration of one 20 mg tablet or capsule. To achieve a target dose of 100 mg would require administration of one 80 mg capsule or tablet and one 20 mg capsule or tablet. To achieve a target dose of 80 mg would require administration of one 80 mg capsule or tablet. To achieve a target dose of 60 mg would require administration of three 20 mg capsules or tablets.

In one embodiment, 60 mg of compound 1 is administered once daily to a patient with cancer in need of treatment. To achieve a dose of 60 mg of compound 1, a patient is administered three 20 mg tablets. The three 20 mg tablets can be taken at the same time or sequentially. In a further embodiment, compound 1 is orally administered with fasting (that is, without eating) for approximately two hours before and 1 hour after administration. Compound 1 is preferably administered with a glass of water (approximately 8 ounces/240 mL).

In another embodiment, 40 mg of compound 1 is administered once daily to a patient with cancer in need of treatment. To achieve a dose of 40 mg of compound 1, a patient is administered two 20 mg tablets. The two 20 mg tablets can be taken at the same time or sequentially. In a further embodiment, compound 1 is orally administered with fasting (that is, without eating) for approximately two hours before and 1 hour after administration. Compound 1 is preferably administered with a glass of water (approximately 8 ounces/240 mL).

In one embodiment, 20 mg of compound 1 is administered once daily to a patient with cancer in need of treatment. To achieve a dose of 20 mg of compound 1, a patient is administered one 20 mg tablet. In a further embodiment, compound 1 is orally administered with fasting (that is, without eating) for approximately two hours before and 1 hour after administration. Compound 1 is preferably administered with a glass of water (approximately 8 ounces/240 mL).

In another embodiment, compound 1 is administered as its free base or malate salt orally once daily as a tablet or capsule as provided in the following table.

| Ingredient | (% w/w) |
|---|---|
| Compound 1 | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00 |

In another embodiment, compound 1 is administered orally as its free base or malate salt once daily as a tablet or capsule as provided in the following table.

| Ingredient | (% w/w) |
|---|---|
| Compound 1 | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100 |

In another embodiment, compound 1 is administered orally as its free base or malate salt once daily as a tablet or capsule as provided in the following table.

| Ingredient | Theoretical Quantity (mg/unit dose) |
|---|---|
| Compound 1 | 100.0 |
| Microcrystalline Cellulose PH-102 | 155.4 |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416 |

In another embodiment, compound 1 is administered orally as its free base or malate salt once daily as a tablet or capsule as provided in the following table.

| Ingredient | Function | % w/w |
|---|---|---|
| Compound 1 | Active Ingredient | 31.7 |
| Microcrystalline Cellulose (Avicel PH-102) | Filler | 38.9 |
| Lactose Anhydrous (60M) | Filler | 19.4 |
| Hydroxypropyl Cellulose (EXF) | Binder | 3.0 |
| Croscarmellose Sodium (Ac-Di-Sol) | Disenegrant | 6.0 |
| Colloidal Silicon Dioxide, | Glidant | 0.3 |
| Magnesium Stearate | Lubricant | 0.75 |
| Opadry Yellow Film Coating which includes: | | |
| HPMC 2910/Hypromellose 6 cp Titanium dioxide Triacetin Iron Oxide Yellow | Film Coating | 4.00 |

Any of the tablet or capsule formulations provided above can be adjusted according to the dose of compound 1 desired. Thus, the amount of each of the formulation ingredients can be proportionally adjusted to provide a table formulation containing various amounts of compound 1 as provided in the previous paragraphs. In another embodiment, the formulations can contain 20, 40, 60, or 80 mg of compound 1.

In one aspect, the pharmaceutical dosage comprising 60 mg of compound 1 is administered to a patient that had one or more adverse event at a dosage greater than 60 mg of compound 1.

In some embodiments, 60 mg of compound 1 is administered to a patient that had one or more adverse event at a pharmaceutical dosage between 80 mg and 160 mg.

In one embodiment, 60 mg of compound 1 is administered to a patient that had one or more adverse event at a dosage of 70 mg of compound 1.

In one embodiment, 60 mg of compound 1 is administered to a patient that had one or more adverse event at a dosage of 80 mg of compound 1.

In one embodiment, 60 mg of compound 1 is administered to a patient that had one or more adverse event at a dosage of 90 mg of compound 1.

In one embodiment, 60 mg of compound 1 is administered to a patient that had one or more adverse event at a dosage of 100 mg of compound 1.

In one embodiment, 60 mg of compound 1 is administered to a patient that had one or more adverse event at a dosage of 120 mg of compound 1.

In one embodiment, 60 mg of compound 1 is administered to a patient that had one or more adverse event at a dosage of 130 mg of compound 1.

In one embodiment, 60 mg of compound 1 is administered to a patient that had one or more adverse event at a dosage of 140 mg of compound 1.

In one embodiment, 60 mg of compound 1 is administered to a patient that had one or more adverse event at a dosage of 150 mg of compound 1.

In one embodiment, 60 mg of compound 1 is administered to a patient that had one or more adverse event at a dosage of 160 mg of compound 1.

In other embodiments, 60 mg of compound 1 is administered to a patient that had one or more adverse event at a pharmaceutical dosage of 140 mg or 100 mg.

In one aspect, the pharmaceutical dosage comprising 40 mg of compound 1 is administered to a patient that had one or more adverse event at a dosage greater than 40 mg of compound 1.

In some embodiments, 40 mg of compound 1 is administered to a patient that had one or more adverse event at a pharmaceutical dosage between 60 mg and 160 mg.

In one embodiment, 40 mg of compound 1 is administered to a patient that had one or more adverse event at a dosage of 50 mg of compound 1.

In one embodiment, 40 mg of compound 1 is administered to a patient that had one or more adverse event at a dosage of 60 mg of compound 1.

In one embodiment, 40 mg of compound 1 is administered to a patient that had one or more adverse event at a dosage of 70 mg of compound 1.

In one embodiment, 40 mg of compound 1 is administered to a patient that had one or more adverse event at a dosage of 80 mg of compound 1.

In one embodiment, 40 mg of compound 1 is administered to a patient that had one or more adverse event at a dosage of 90 mg of compound 1.

In one embodiment, 40 mg of compound 1 is administered to a patient that had one or more adverse event at a dosage of 100 mg of compound 1.

In one embodiment, 40 mg of compound 1 is administered to a patient that had one or more adverse event at a dosage of 120 mg of compound 1.

In one embodiment, 40 mg of compound 1 is administered to a patient that had one or more adverse event at a dosage of 130 mg of compound 1.

In one embodiment, 40 mg of compound 1 is administered to a patient that had one or more adverse event at a dosage of 140 mg of compound 1.

In one embodiment, 40 mg of compound 1 is administered to a patient that had one or more adverse event at a dosage of 150 mg of compound 1.

In one embodiment, 40 mg of compound 1 is administered to a patient that had one or more adverse event at a dosage of 160 mg of compound 1.

In other embodiment, 40 mg of compound 1 is administered to a patient that had one or more adverse event at a pharmaceutical dosage of 140 mg, 100 mg, or 60 mg.

In one aspect, the pharmaceutical dosage comprising 20 mg of compound 1 is administered to a patient that had one or more adverse event at a dosage greater than 60 mg of compound 1.

In some embodiments, 20 mg of compound 1 is administered to a patient that had one or more adverse event at a pharmaceutical dosage between 40 mg and 160 mg.

In one embodiment, 20 mg of compound 1 is administered to a patient that had one or more adverse event at a dosage of 30 mg of compound 1.

In one embodiment, 20 mg of compound 1 is administered to a patient that had one or more adverse event at a dosage of 40 mg of compound 1.

In one embodiment, 20 mg of compound 1 is administered to a patient that had one or more adverse event at a dosage of 50 mg of compound 1.

In one embodiment, 20 mg of compound 1 is administered to a patient that had one or more adverse event at a dosage of 60 mg of compound 1.

In one embodiment, 20 mg of compound 1 is administered to a patient that had one or more adverse event at a dosage of 70 mg of compound 1.

In one embodiment, 20 mg of compound 1 is administered to a patient that had one or more adverse event at a dosage of 80 mg of compound 1.

In one embodiment, 20 mg of compound 1 is administered to a patient that had one or more adverse event at a dosage of 90 mg of compound 1.

In one embodiment, 20 mg of compound 1 is administered to a patient that had one or more adverse event at a dosage of 100 mg of compound 1.

In one embodiment, 20 mg of compound 1 is administered to a patient that had one or more adverse event at a dosage of 120 mg of compound 1.

In one embodiment, 20 mg of compound 1 is administered to a patient that had one or more adverse event at a dosage of 130 mg of compound 1.

In one embodiment, 20 mg of compound 1 is administered to a patient that had one or more adverse event at a dosage of 140 mg of compound 1.

In one embodiment, 20 mg of compound 1 is administered to a patient that had one or more adverse event at a dosage of 150 mg of compound 1.

In one embodiment, 20 mg of compound 1 is administered to a patient that had one or more adverse event at a dosage of 160 mg of compound 1.

In other embodiments, 20 mg of compound 1 is administered to a patient that had one or more adverse event at a pharmaceutical dosage of 140 mg, 100 mg, 60 mg, or 40 mg.

In some embodiments, the adverse event is one or more of diarrhea, stomatitis, palmar-plantar erythrodysesthesia syndrome (PPES), decreased weight, decreased appetite, nausea, fatigue, oral pain, hair color changes, dysgeusia, hypertension, abdominal pain, constipation, increased AST, increased ALT, lymphopenia, increased alkaline phosphatase, hypocalcemia, neutropenia, thrombocytopenia, hypophosphatemia, hyperbilirubinemia, perforations, fistulas, hemorrhage, thromboembolic events, wound complications, osteonecrosis of the jaw, proteinuria, reversible posterior leukoencephalopathy syndrome (RPLS), and embryo-fetal toxicity.

In some embodiments, the adverse event is Grade 1. In some embodiments, the adverse event is Grade 2. In some embodiments, the adverse event is Grade 3. In some embodiments, the adverse event is Grade 4. In some embodiments, the adverse event is Grade 5.

In one embodiment, treatment is temporarily suspended for a patient who had a Grade 4 adverse event. In another embodiment, upon resolution or improvement of the Grade 4 adverse event, the dose of compound 1 is resumed at the same or a reduced dosage. In some embodiments, resolution or improvement of the Grade 4 adverse event means returning to baseline. In other embodiments, resolution or improvement of the Grade 4 adverse event means resolution to a Grade 1 adverse event.

In one embodiment, treatment is temporarily suspended for a patient who had a Grade 3 adverse event. In another embodiment, upon resolution or improvement of the Grade 3 adverse event, the dose of compound 1 is resumed at the same or a reduced dosage. In some embodiments, resolution or improvement of the Grade 3 adverse event means returning to baseline. In other embodiments, resolution or improvement of the Grade 4 adverse event means resolution to a Grade 1 adverse event.

In one embodiment, treatment is temporarily suspended for a patient who had a Grade 2 adverse event. In another embodiment, upon resolution or improvement of the Grade 2 adverse event, the dose of compound 1 is resumed at the same or a reduced dosage. In some embodiments, resolution or improvement of the Grade 2 adverse event means returning to baseline. In other embodiments, resolution or improvement of the Grade 2 adverse event means resolution to a Grade 1 adverse event.

In one embodiment, treatment is temporarily suspended for a patient who had a Grade 1 adverse event. In another embodiment, upon resolution or improvement of the Grade 4 adverse event, the dose of compound 1 is resumed at the same or a reduced dosage. In some embodiments, resolution or improvement of the Grade 1 adverse event means returning to baseline.

In some embodiments, the dose is further reduced one or more times following the first reduction as a result of one or more adverse events. In one embodiment, the dose is reduced a first time. In another embodiment, the dose is reduced a first and second time. In another embodiment, the dose is reduced a first, second, and third time.

In some embodiments, the dose is further reduced to 140 mg. In some embodiments, the dose is further reduced to 120 mg. In some embodiments, the dose is further reduced to 100 mg. In some embodiments, the dose is further reduced to 80 mg. In some embodiments, the dose is further reduced to 60 mg. In some embodiments, the dose is further reduced to 40 mg. In some embodiments, the dose is further reduced to 20 mg.

In another aspect, the invention is directed to a pharmaceutical dosage comprising 60 mg of compound 1:

Compound 1 or a pharmaceutically acceptable salt thereof or a pharmaceutical composition comprising compound 1 and a pharmaceutically acceptable carrier is administered orally with fasting as its free base or malate salt once daily as a tablet or capsule. In some embodiments, compound 1 is administered as a tablet. In other embodiments, compound 1 is administered as a capsule.

In another aspect, the invention is directed to a pharmaceutical dosage comprising 40 mg of compound 1:

Compound 1 or a pharmaceutically acceptable salt thereof or a pharmaceutical composition comprising compound 1 and a pharmaceutically acceptable carrier is administered orally with fasting as its free base or malate salt once daily as a tablet or capsule. In some embodiments, compound 1 is administered as a tablet. In other embodiments, compound 1 is administered as a capsule.

In another aspect, the invention is directed to a pharmaceutical dosage comprising 20 mg of compound 1:

Compound 1 or a pharmaceutically acceptable salt thereof or a pharmaceutical composition comprising compound 1 and a pharmaceutically acceptable carrier is administered orally with fasting as its free base or malate salt once daily as a tablet or capsule. In some embodiments, compound 1 is administered as a tablet. In other embodiments, compound 1 is administered as a capsule.

In another aspect, the invention is directed to a method of treating cancer, comprising: administering a pharmaceutical dosage comprising 60 mg of compound 1:

Compound 1 or a pharmaceutically acceptable salt thereof or a pharmaceutical composition comprising compound 1 and a pharmaceutically acceptable carrier.

In another aspect, the invention is directed to a method of treating cancer, comprising: administering a pharmaceutical dosage comprising 40 mg of compound 1:

Compound 1 or a pharmaceutically acceptable salt thereof or a pharmaceutical composition comprising compound 1 and a pharmaceutically acceptable carrier.

In another aspect, the invention is directed to a method of treating cancer, comprising: administering a pharmaceutical dosage comprising 20 mg of compound 1:

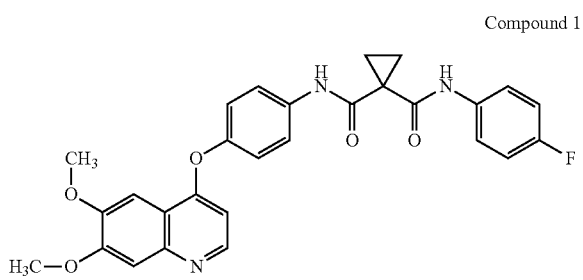 [SMILES: COc1cc2nccc(Oc3ccc(NC(=O)C4(C(=O)Nc5ccc(F)cc5)CC4)cc3)c2cc1OC]

Compound 1 or a pharmaceutically acceptable salt thereof or a pharmaceutical composition comprising compound 1 and a pharmaceutically acceptable carrier.

In another embodiment of each aspect, the method comprises administering compound 1 as the malate salt.

In some embodiments, the method comprises administering compound 1 as the (R)-malate salt.

In other embodiments, the method comprises administering compound 1 as the (S)-malate salt.

In another embodiment, the method comprises administering the malate salt as the crystalline N-1 form of the (S) malate salt and/or the (R) malate salt of the compound 1 as disclosed in U.S. Patent Application Ser. No. 61/325,095. Also see WO 2008/083319 for the properties of crystalline enantiomers, including the N-1 and/or the N-2 crystalline forms of the malate salt of compound 1, which is incorporated herein by reference in its entirety. Methods of making and characterizing such forms are fully described in PCT/US10/21194, which is incorporated herein by reference in its entirety.

In one embodiment, the method comprises administering compound 1 as a tablet or capsule containing compound 1 as the S-malate salt and pharmaceutically acceptable carriers and excipients. In some embodiments, compound 1 is administered as a tablet. In other embodiments, compound 1 is administered as a capsule.

In this method, the desired dosage of compound 1 can be achieved using a combination of tablets or capsules as needed. For example to achieve a target dose of 20 mg would require administration of one 20 mg tablet or capsule. To achieve a target dose of 100 mg would require administration of one 80 mg tablet or capsule and one 20 mg tablet or capsule. To achieve a target dose of 80 mg would require administration of one 80 mg tablet or capsule. To achieve a target dose of 60 mg would require administration of three 20 mg tablets or capsules.

In a preferred embodiment of this method, 60 mg of compound 1 is administered once daily to a patient with cancer in need of treatment. To achieve a dose of 60 mg of compound 1, a patient is administered three 20 mg tablets. The three 20 mg tablets can be taken at the same time or sequentially. In a further embodiment, compound 1 is orally administered with fasting (that is, without eating) for approximately two hours before and 1 hour after administration. Compound 1 is preferably administered with a glass of water (approximately 8 ounces/240 mL).

In a preferred embodiment of this method, 40 mg of compound 1 is administered once daily to a patient with cancer in need of treatment. To achieve a dose of 40 mg of compound 1, a patient is administered two 20 mg tablets. The two 20 mg tablets can be taken at the same time or sequentially. In a further embodiment, compound 1 is orally administered with fasting (that is, without eating) for approximately two hours before and 1 hour after administration. Compound 1 is preferably administered with a glass of water (approximately 8 ounces/240 mL).

In a preferred embodiment of this method, 20 mg of compound 1 is administered once daily to a patient with cancer in need of treatment. To achieve a dose of 20 mg of compound 1, a patient is administered one 20 mg tablet. In a further embodiment, compound 1 is orally administered with fasting (that is, without eating) for approximately two hours before and 1 hour after administration. Compound 1 is preferably administered with a glass of water (approximately 8 ounces/240 mL).

In another embodiment, the method comprises administering compound 1 as its free base or malate salt orally once daily as a tablet or capsule as provided in the following table.

| Ingredient | (% w/w) |
| --- | --- |
| Compound 1 | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00 |

In some embodiments, compound 1 is administered as a tablet. In other embodiments, compound 1 is administered as a capsule.

In another embodiment, the method comprises administering compound 1 orally as its free base or malate salt once daily as a tablet or capsule as provided in the following table.

| Ingredient | (% w/w) |
| --- | --- |
| Compound 1 | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100 |

In some embodiments, compound 1 is administered as a tablet. In other embodiments, compound 1 is administered as a capsule.

In another embodiment, the method comprises administering compound 1 orally as its free base or malate salt once daily as a tablet or capsule as provided in the following table.

| Ingredient | Theoretical Quantity (mg/unit dose) |
| --- | --- |
| Compound 1 | 100.0 |
| Microcrystalline Cellulose PH-102 | 155.4 |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416 |

In some embodiments, compound 1 is administered as a tablet. In other embodiments, compound 1 is administered as a capsule.

In another embodiment, the method comprises administering compound 1 orally as its free base or malate salt once daily as a tablet or capsule as provided in the following table.

| Ingredient | Function | % w/w |
|---|---|---|
| Compound 1 | Active Ingredient | 31.7 |
| Microcrystalline Cellulose (Avicel PH-102) | Filler | 38.9 |
| Lactose Anhydrous (60M) | Filler | 19.4 |
| Hydroxypropyl Cellulose (EXF) | Binder | 3.0 |
| Croscarmellose Sodium (Ac-Di-Sol) | Disenegrant | 6.0 |
| Colloidal Silicon Dioxide, | Glidant | 0.3 |
| Magnesium Stearate | Lubricant | 0.75 |
| Opadry Yellow Film Coating which includes: | | |
| HPMC 2910/Hypromellose 6 cp | | |
| Titanium dioxide | Film Coating | 4.00 |
| Triacetin | | |
| Iron Oxide Yellow | | |

In some embodiments, compound 1 is administered as a tablet. In other embodiments, compound 1 is administered as a capsule.

In another aspect, the invention is directed to a method of treating cancer, comprising administering to a patient in need of such treatment a pharmaceutical dosage comprising 60 mg of compound 1:

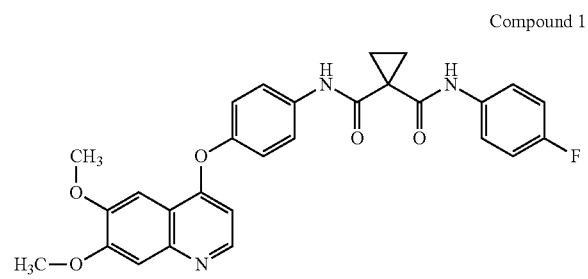 [SMILES: COc1cc2nccc(Oc3ccc(NC(=O)C4(C(=O)Nc5ccc(F)cc5)CC4)cc3)c2cc1OC]

Compound 1 or a pharmaceutically acceptable salt thereof or a pharmaceutical composition comprising compound 1 and a pharmaceutically acceptable carrier is administered orally with fasting as its free base or malate salt once daily as a tablet or capsule. In some embodiments, compound 1 is administered as a tablet. In other embodiments, compound 1 is administered as a capsule.

In another aspect, the invention is directed to a method of treating cancer, comprising administering to a patient in need of such treatment a pharmaceutical dosage comprising 40 mg of compound 1:

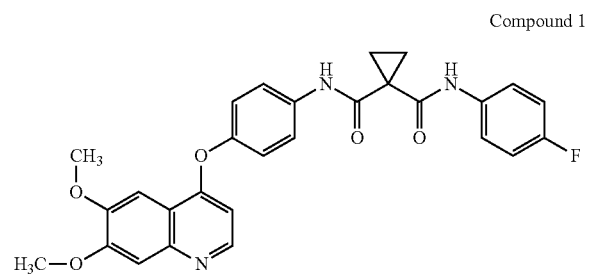 [SMILES: COc1cc2nccc(Oc3ccc(NC(=O)C4(C(=O)Nc5ccc(F)cc5)CC4)cc3)c2cc1OC]

Compound 1 or a pharmaceutically acceptable salt thereof or a pharmaceutical composition comprising compound 1 and a pharmaceutically acceptable carrier is administered orally with fasting as its free base or malate salt once daily as a tablet or capsule. In some embodiments, compound 1 is administered as a tablet. In other embodiments, compound 1 is administered as a capsule.

In another aspect, the invention is directed to a method of treating cancer, comprising administering to a patient in need of such treatment a pharmaceutical dosage comprising 20 mg of compound 1:

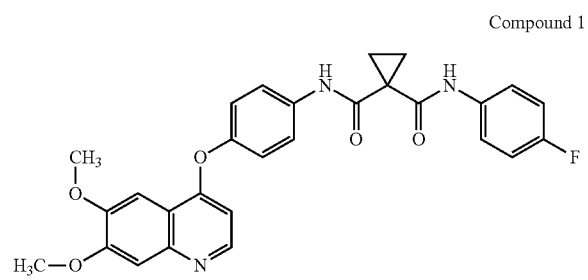 [SMILES: COc1cc2nccc(Oc3ccc(NC(=O)C4(C(=O)Nc5ccc(F)cc5)CC4)cc3)c2cc1OC]

Compound 1 or a pharmaceutically acceptable salt thereof or a pharmaceutical composition comprising compound 1 and a pharmaceutically acceptable carrier is administered orally with fasting as its free base or malate salt once daily as a tablet or capsule. In some embodiments, compound 1 is administered as a tablet. In other embodiments, compound 1 is administered as a capsule.

Any of the capsule formulations provided above can be adjusted according to the dose of compound 1 desired. Thus, the amount of each of the formulation ingredients can be proportionally adjusted to provide a table formulation containing various amounts of compound 1 as provided in the previous paragraphs. In another embodiment, the formulations can contain 20, 40, 60, or 80 mg of compound 1.

In some embodiments, the cancer to be treated is thyroid cancer, liver cancer, gastrointestinal cancer, pancreatic cancer, bone cancer, hematologic cancer, skin cancer, kidney cancer, breast cancer, colon cancer, fallopian tube cancer, ovarian cancer, brain cancer, lung cancer, or prostate cancer.

In one embodiment, the cancer is thyroid cancer.

More particularly, the thyroid cancer is medullary thyroid cancer.

In one embodiment, the cancer in liver cancer.

More particularly, the liver cancer is hepatocellular carcinoma, cholangiocarcinoma, hepatoblastoma, angiosarcoma, hepatocellular adenoma, or hemangioma.

In one embodiment, the cancer is gastrointestinal cancer.

More particularly, the gastrointestinal cancer is cancer of the esophagus which is squamous cell carcinoma, adenocarcinoma, or leiomyosarcoma; cancer of the stomach which is carcinoma, or lymphoma; cancer of the pancreas, which is ductal adenocarcinoma, insulinoma, gucagonoma, gastrinoma, carcinoid tumors, or vipoma; cancer of the small bowel, which is adenocarcinoma, lymphoma, carcinoid tumors, Karposi's sarcoma, leiomyoma, hemangioma, lipoma; or cancer of the large bowel, which is adenocarcinoma, tubular adenoma, villous adenoma, hamartoma, or leiomyoma.

In one embodiment, the cancer is cancer of the pancreas.

More particularly, the cancer of the pancreas is ductal adenocarcinoma, insulinoma, gucagonoma, gastrinoma, carcinoid tumors, or vipoma.

In one embodiment, the cancer is bone cancer.

More particularly, the bone cancer is osteosarcoma, fibrosarcoma, malignant fibrous histiocytoma, chondrosarcoma, Ewing's sarcoma, malignant reticulum cell sarcoma, malignant giant cell tumor chordoma, osteocartiliginous exostoses, chondroblastoma, chondromyofibroma, or osteoid osteoma.

In one embodiment, the cancer is hematologic cancer.

More particularly, the hematologic cancer is myeloid leukemia, acute lymphoblastic leukemia, chronic lymphocytic leukemia, myeloproliferative diseases, multiple myeloma, or myelodysplastic syndrome.

In one embodiment, the cancer is skin cancer.

More particularly, the skin cancer is malignant melanoma, basal cell carcinoma, squamous cell carcinoma, or Karposi's sarcoma.

In one embodiment, the cancer is renal cancer.

More particularly, the renal cancer is a renal tumor.

In one embodiment, the cancer is breast cancer.

More particularly, the breast cancer is a breast tumor.

In one embodiment, the cancer is colon cancer.

More particularly, the colon cancer is a colon cancer tumor.

In one embodiment, the cancer is fallopian tube cancer.

More particularly, the fallopian tube cancer is fallopian tube carcinoma.

In one embodiment, the cancer is ovarian cancer.

More particularly, the ovarian cancer is ovarian carcinoma [serous cystadenocarcinoma, mucinous cystadenocarcinoma, unclassified carcinoma], granulosa-thecal cell tumors, Sertoli Leydig cell tumors, dysgerminoma, malignant teratoma), vulva (squamous cell carcinoma, intraepithelial carcinoma, adenocarcinoma, fibrosarcoma, or melanoma.

In another embodiment, the cancer is prostate cancer.

More particularly, the prostate cancer is adenocarcinoma or sarcoma.

In another embodiment, the prostate cancer is castration resistant prostate cancer (CRPC).

In another embodiment, the cancer is lung cancer.

More particularly, the lung cancer is bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, or inesothelioma.

The antitumor effect of the dosage form of the invention is measured using serological and/or radiographic methods available to the skilled practitioner. For serological methods, the relative concentration of a cancer biomarker is measured before and after administration of compound 1. A positive response means that there is a lower serological concentration of the biomarker after treatment as compared to the concentration before treatment. As an example, for patients being treated for prostate cancer, particularly castration-resistant prostate cancer, the serological concentration of the biomarker PSA will be determined before, during, and after treatment. Patients can be assigned a PSA response according to the following criteria:

Complete Serological Response: PSA level less than 0.2 ng/mL measured for 2 consecutive measurements at least 4 weeks apart.

Serological Partial Response (PR): decline of PSA value, referenced to the pre-study level, by greater than or equal to 50% for 2 consecutive measurements at least 2 weeks apart.

PSA Stable Disease: Patients who do not meet the criteria for response (CR or PR) or serological progression Serological Progression (PD): is observed when the PSA demonstrates an increase that is more than 50% of nadir, taking as reference the lowest recorded PSA level since starting therapy. Two consecutive increases must be documented with each measurement obtained at least 2 weeks apart. On occasions, there may be an intermediate fluctuant value. In accordance with the Recommendations of the Prostate Cancer Clinical Trials Working Group this will not restart the evaluation period so long as the intermediate value was not below the previous nadir[18]. The date of first recorded increase (not defeated by a subsequent drop in PSA level to create a new nadir) will be deemed the date of progression. If a patient achieves a PSA that is less than 2 ng/mL, progression will only be deemed to have been confirmed once: (1) There has been an observed rise that is more than 50% of nadir since starting ADT; AND (2) The confirming increase was to a value that is more than 2.0 ng/mL (the unconfirmed and second increase may be a value that is less than 2.0 ng/mL but greater than 50% of nadir since starting ADT).

These serological response levels can be modified as needed based on the biomarker at issue.

In one embodiment, a complete serological response is observed in patients being treated with the dosage form. In another embodiment, a serological partial response is observed in patients being treated with the dosage form. In a further embodiment, stable disease is observed in patients being treated with the dosage form.

With respect to radiographic methods, radiographic disease progression is defined by RECIST 1.1 for soft tissue disease, or the appearance of two or more new bone lesions on bone scan. Progression in the absence of clear symptomatic worsening at the first scheduled reassessment after commencement of treatment requires a confirmatory scan at later point in time. Standard imaging procedures available to the skilled practitioner, including technetium bone scans and CT scans can be used to measure radiographic effect. Other radiographic methods such as NaF and FDG-PET may also be used to measure radiographic effect.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions can include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

EMBODIMENTS

Embodiment 1

A pharmaceutical dosage comprising 60 mg, 40 mg, or 20 mg of compound 1:

Compound 1 or a pharmaceutically acceptable salt thereof or a pharmaceutical composition comprising compound 1 and a pharmaceutically acceptable carrier.

Embodiment 2

The pharmaceutical dosage of embodiment 1, wherein compound 1 is the malate salt.

Embodiment 3

The pharmaceutical dosage of embodiments 1-2, wherein compound 1 is the (R)-malate salt.

Embodiment 4

The pharmaceutical dosage of embodiments 1-3, wherein compound 1 is the (S)-malate salt.

Embodiment 5

The pharmaceutical dosage of embodiments 1-4, wherein compound 1 is the crystalline N-1 form of the (S)-malate salt.

Embodiment 6

The pharmaceutical dosage of embodiments 1-5, wherein compound 1 is the crystalline N-1 form of the (R)-malate salt.

Embodiment 7

The pharmaceutical dosage of embodiments 1-6, wherein compound 1 is a solid dosage form for oral administration.

Embodiment 8

The pharmaceutical dosage of embodiments 1-7, wherein compound 1 is administered as a capsule or tablet.

Embodiment 9

The pharmaceutical dosage of embodiments 1-9, wherein the dose of 60 mg is administered as three 20 mg tablets.

Embodiment 10

The pharmaceutical dosage of embodiments 1-9, wherein the dose of 40 mg is administered as two 20 mg tablets.

Embodiment 11

The pharmaceutical dosage of embodiments 1-10, wherein the dose of 20 mg is administered as one 20 mg tablet.

Embodiment 12

The pharmaceutical dosage of embodiments 1-11, wherein the dose of compound 1 is administered once daily at the same time or sequentially.

Embodiment 13

The pharmaceutical dosage of embodiments 1-12, wherein the dose of compound 1 is orally administered with fasting for approximately two hours before and 1 hour after administration.

Embodiment 14

The pharmaceutical dosage of embodiments 1-13, wherein the dose of compound 1 is administered with approximately 8 ounces (240 mL) of water.

Embodiment 15

The pharmaceutical dosage of embodiments 1-14, wherein 60 mg of compound 1 is administered to a patient that had one or more adverse event at a pharmaceutical dosage greater than 60 mg.

Embodiment 16

The pharmaceutical dosage of embodiments 1-15, wherein 40 mg of compound 1 is administered to a patient that had one or more adverse event at a pharmaceutical dosage greater than 40 mg.

Embodiment 17

The pharmaceutical dosage of embodiments 1-16, wherein 20 mg of compound 1 is administered to a patient that had one or more adverse event at a pharmaceutical dosage greater than 20 mg.

Embodiment 18

The pharmaceutical dosage of embodiments 1-17, wherein the adverse event is one or more of diarrhea, stomatitis, palmar-plantar erythrodysesthesia syndrome (PPES), decreased weight, decreased appetite, nausea, fatigue, oral pain, hair color changes, dysgeusia, hypertension, abdominal pain, constipation, increased AST, increased ALT, lymphopenia, increased alkaline phosphatase, hypocalcemia, neutropenia, thrombocytopenia, hypophosphatemia, hyperbilirubinemia, perforations, fistulas, hemorrhage, thromboembolic events, wound complications, osteonecrosis of the jaw, proteinuria, reversible posterior leukoencephalopathy syndrome (RPLS), and embryofetal toxicity.

Embodiment 19

The pharmaceutical dosage of embodiments 1-18, wherein compound 1 is administered as one, two, or three 20 mg tablets comprising:

| Ingredient | Function | % w/w |
|---|---|---|
| Compound 1 | Active Ingredient | 31.7 |
| Microcrystalline Cellulose (Avicel PH-102) | Filler | 38.9 |
| Lactose Anhydrous (60M) | Filler | 19.4 |
| Hydroxypropyl Cellulose (EXF) | Binder | 3.0 |
| Croscarmellose Sodium (Ac-Di-Sol) | Disenegrant | 6.0 |
| Colloidal Silicon Dioxide, | Glidant | 0.3 |
| Magnesium Stearate | Lubricant | 0.75 |
| Opadry Yellow Film Coating which includes: | | |
| HPMC 2910/Hypromellose 6 cp | | |
| Titanium dioxide | Film Coating | 4.00 |
| Triacetin | | |
| Iron Oxide Yellow | | |

Embodiment 20

A method of treating cancer comprising administering a pharmaceutical dosage comprising 60 mg, 40 mg, or 20 mg of compound 1:

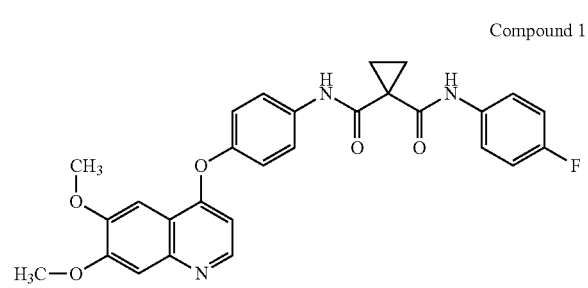

Compound 1 or a pharmaceutically acceptable salt thereof or a pharmaceutical composition comprising compound 1 and a pharmaceutically acceptable carrier.

Embodiment 21

The method of embodiment 20, wherein the cancer is selected from thyroid cancer, liver cancer, gastrointestinal cancer, pancreatic cancer, bone cancer, hematologic cancer, skin cancer, kidney cancer, breast cancer, colon cancer, fallopian tube cancer, ovarian cancer, brain cancer, lung cancer, and prostate cancer.

Embodiment 22

The method of embodiments 20-21, wherein the 60 mg of compound 1 is administered to a patient that had one or more adverse event at a pharmaceutical dosage greater than 60 mg.

Embodiment 23

The method of embodiments 20-22, wherein the 40 mg of compound 1 is administered to a patient that had one or more adverse event at a pharmaceutical dosage greater than 40 mg.

Embodiment 24

The method of embodiments 20-23, wherein the 20 mg of compound 1 is administered to a patient that had one or more adverse event at a pharmaceutical dosage greater than 20 mg.

Embodiment 25

The method of embodiments 20-24, wherein the cancer is prostate cancer.

Embodiment 26

The method of embodiments 20-25, wherein the cancer is castration resistant prostate cancer.

Embodiment 27

The method of embodiments 20-26, wherein compound 1 is administered as one, two, or three 20 mg tablets comprising:

| Ingredient | Function | % w/w |
|---|---|---|
| Compound 1 | Active Ingredient | 31.7 |
| Microcrystalline Cellulose (Avicel PH-102) | Filler | 38.9 |
| Lactose Anhydrous (60M) | Filler | 19.4 |
| Hydroxypropyl Cellulose (EXF) | Binder | 3.0 |
| Croscarmellose Sodium (Ac-Di-Sol) | Disenegrant | 6.0 |
| Colloidal Silicon Dioxide, | Glidant | 0.3 |
| Magnesium Stearate | Lubricant | 0.75 |
| Opadry Yellow Film Coating which includes: | | |
| HPMC 2910/Hypromellose 6 cp | | |
| Titanium dioxide | Film Coating | 4.00 |
| Triacetin | | |
| Iron Oxide Yellow | | |

Preparation of Compound 1

Preparation of
1-(4-Fluorophenylcarbamoyl)cyclopropanecarboxylic acid (Compound A-1)

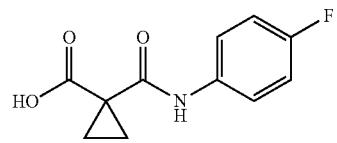 [SMILES: O=C(O)C1(C(=O)Nc2ccc(F)cc2)CC1]

The starting 1,1-cyclopropanedicarboxylic acid was treated with thionyl chloride (1.05 equivalents) in approximately 8 volumes of isopropyl acetate at 25° C. for 5 hours. The resulting mixture was then treated with a solution of 4-fluoroaniline (1.1 equivalents) and triethylamine (1.1 equivalents) in isopropyl acetate (2 volumes) over 1 hour.

The product slurry was quenched with 5N NaOH solution (5 volumes), and the aqueous phase was discarded. The organic phase was extracted with 0.5N NaOH solution (10 volumes), and the basic extract was washed with heptane (5 volumes) and subsequently acidified with 30% HCl solution to give a slurry. Compound A-1 was isolated by filtration.

Compound A-1 was prepared on a 1.00 kg scale using 1,1-cyclopropanedicarboxylic acid as the limiting reagent to furnish 1.32 kg of Compound A-1 (77% isolated yield; 84% mass balance) with 99.92% purity (HPLC) and 100.3% assay.

Preparation of N-(4-{[6,7-bis(methyloxy)quinolin-4-yl]oxy}phenyl)-N'-(4-fluorophenyl)cyclopropane-1,1-dicarboxamide (Compound 1) and the (S)-malate salt thereof A synthetic route that can be used for the preparation of N-(4-{[6,7-bis(methyloxy)quinolin-4-yl]oxy}phenyl)-N'-(4-fluorophenyl)cyclopropane-1,1-dicarboxamide and the (S)-malate salt thereof is depicted in Scheme 1.

Scheme 1

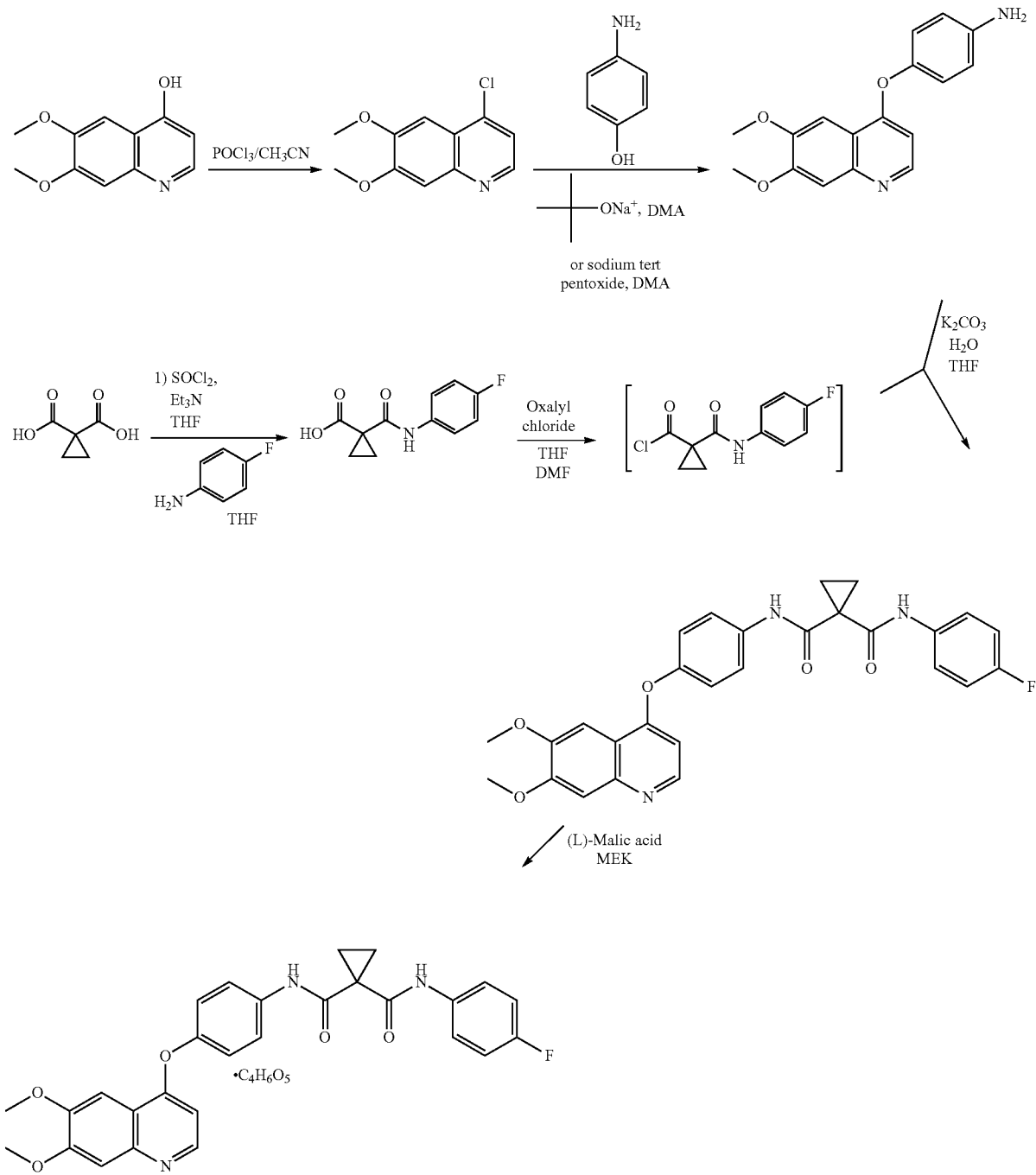

Another synthetic route that can be used for the preparation of N-(4-{[6,7-bis(methyloxy)quinolin-4-yl]oxy}phenyl)-N'-(4-fluorophenyl)cyclopropane-1,1-dicarboxamide and the (S)-malate salt thereof is depicted in Scheme 2.

the addition of POCl₃, the temperature of the reaction mixture was raised to approximately 77° C. The reaction was deemed complete (approximately 13 hours) when less than 3% of the starting material remained, as measured by in-process high-performance liquid chromatography

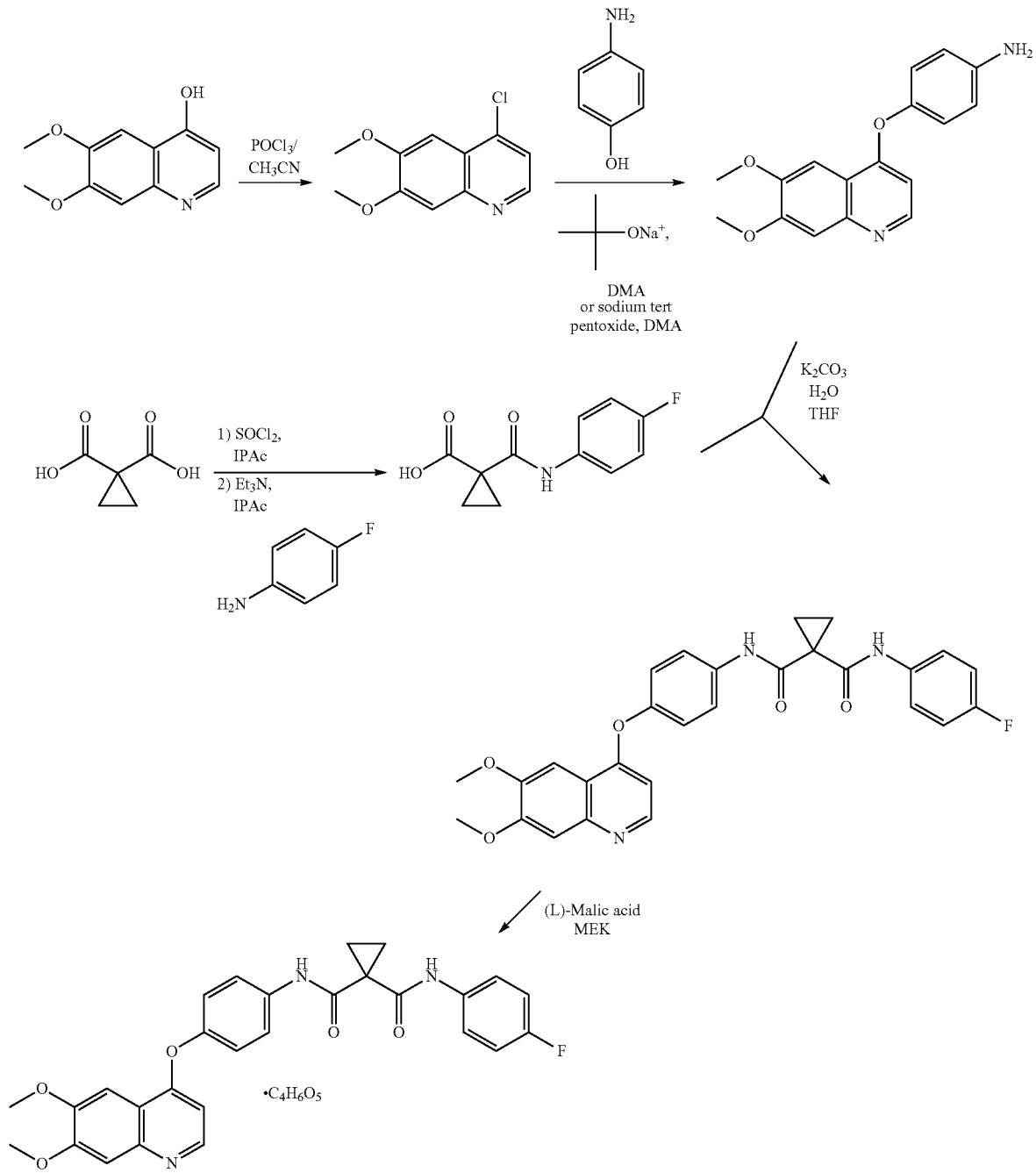

Preparation of 4-Chloro-6,7-dimethoxy-quinoline

A reactor was charged sequentially with 6,7-dimethoxy-quinoline-4-ol (47.0 kg) and acetonitrile (318.8 kg). The resulting mixture was heated to approximately 60° C., and phosphorus oxychloride (POCl₃, 130.6 kg) was added. After

[HPLC] analysis. The reaction mixture was cooled to approximately 2 to 7° C. and then quenched into a chilled solution of dichloromethane (DCM, 482.8 kg), 26% NH₄OH (251.3 kg), and water (900 L). The resulting mixture was warmed to approximately 20 to 25° C., and phases were separated. The organic phase was filtered through a bed of AW hyflo super-cel NF (Celite; 5.4 kg), and the filter bed was washed with DCM (118.9 kg). The combined organic phase was washed with brine (282.9 kg) and mixed with water (120 L). The phases were separated, and the organic phase was concentrated by vacuum distillation with the removal of solvent (approximately 95 L residual volume). DCM (686.5 kg) was charged to the reactor containing organic phase and concentrated by vacuum distillation with the removal of solvent (approximately 90 L residual volume). Methyl t-butyl ether (MTBE, 226.0 kg) was then charged, and the temperature of the mixture was adjusted to −20 to −25° C. and held for 2.5 hours resulting in solid precipitate, which was then filtered, washed with n-heptane (92.0 kg), and dried on a filter at approximately 25° C. under nitrogen to afford the title compound (35.6 kg).

Preparation of
4-(6,7-Dimethoxy-quinoline-4-yloxy)-phenylamine

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide (21.4 kg), and DMA (167.2 kg) at 20-25° C. This mixture was then heated to 100-105° C. for approximately 13 hours. After the reaction was deemed complete as determined using in-process HPLC analysis (less than 2% starting material remaining), the reactor contents were cooled at 15 to 20° C., and water (pre-cooled, 2 to 7° C., 587 L) was charged at a rate to maintain 15 to 30° C. temperature. The resulting solid precipitate was filtered, washed with a mixture of water (47 L) and DMA (89.1 kg), and finally washed with water (214 L). The filter cake was then dried at approximately 25° C. on filter to yield crude 4-(6,7-dimethoxy-quinoline-4-yloxy)*-phenylamine (59.4 kg wet, 41.6 kg dry calculated based on LOD). Crude 4-(6,7-dimethoxy-quinoline-4-yloxy)-phenylamine was refluxed (approximately 75° C.) in a mixture of tetrahydrofuran (THF, 211.4 kg) and DMA (108.8 kg) for approximately 1 hour, then cooled to 0 to 5° C., and aged for approximately 1 hour, after which time the solid was filtered, washed with THF (147.6 kg), and dried on a filter under vacuum at approximately 25° C. to yield 4-(6,7-dimethoxy-quinoline-4-yloxy)-phenylamine (34.0 kg).

Alternative Preparation of
4-(6,7-Dimethoxy-quinoline-4-yloxy)-phenylamine 4-chloro-6,7-dimethoxyquinoline (34.8 kg), 4-Aminophenol (30.8 kg), and sodium tert pentoxide (1.8 equivalents) 88.7 kg, 35 weight percent in THF) were charged to a reactor, followed by N,N-dimethylacetamide (DMA, 293.3 kg). This mixture was then heated to 105 to 115° C. for approximately 9 hours. After the reaction was deemed complete as determined using in-process HPLC analysis (less than 2% starting material remaining), the reactor contents were cooled at 15 to 25° C., and water (315 kg) was added over a two hour period while maintaining the temperature between 20 and 30° C. The reaction mixture was then agitated for an additional hour at 20 to 25° C. The crude product was collected by filtration and washed with a mixture of 88 kg water and 82.1 kg DMA, followed by 175 kg water. The product was dried on a filter drier for 53 hours. The LOD showed less than 1% w/w.

In an alternative procedure, 1.6 equivalents of sodium tert-pentoxide were used, and the reaction temperature was increased from 110 to 120° C. In addition, the cool down temperature was increased to 35 to 40° C., and the starting temperature of the water addition was adjusted to 35 to 40° C., with an allowed exotherm to 45° C.

Preparation of
1-(4-Fluoro-phenylcarbamoyl)-cyclopropanecarbonyl
chloride

Oxalyl chloride (12.6 kg) was added to a solution of 1-(4-fluoro-phenylcarbamoyl)-cyclopropanecarboxylic acid (22.8 kg) in a mixture of THF (96.1 kg) and N, N-dimethylformamide (DMF; 0.23 kg) at a rate such that the batch temperature did not exceed 25° C. This solution was used in the next step without further processing.

Alternative Preparation of
1-(4-Fluoro-phenylcarbamoyl)-cyclopropanecarbonyl
chloride A reactor was charged with 1-(4-fluoro-phenylcarbamoyl)-cyclopropanecarboxylic acid (35 kg), DMF (344 g), and THF (175 kg). The reaction mixture was adjusted to 12 to 17° C., and then to the reaction mixture was charged 19.9 kg of oxalyl chloride over a period of 1 hour. The reaction mixture was left stirring at 12 to 17° C. for 3 to 8 hours. This solution was used in the next step without further processing.

Preparation of cyclopropane-1,1-dicarboxylic acid
[4-(6,7-dimethoxy-quinoline-4-yloxy)-phenyl]-
amide(4-fluoro-phenyl)-amide The solution from the previous step containing 1-(4-fluoro-phenylcarbamoyl)-cyclopropanecarbonyl chloride was added to a mixture of compound 4-(6,7-dimethoxy-quinoline-4-yloxy)-phenylamine (23.5 kg) and potassium carbonate (31.9 kg) in THF (245.7 kg) and water (116 L) at a rate such that the batch temperature did not exceed 30° C. When the reaction was complete (in approximately 20 minutes), water (653 L) was added. The mixture was stirred at 20 to 25° C. for approximately 10 hours, which resulted in the precipitation of the product. The product was recovered by filtration, washed with a pre-made solution of THF (68.6 kg) and water (256 L), and dried first on a filter under nitrogen at approximately 25° C. and then at approximately 45° C. under vacuum to afford the title compound (41.0 kg, 38.1 kg, calculated based on LOD).

Alternative Preparation of cyclopropane-1,1-dicarboxylic acid [4-(6,7-dimethoxy-quinoline-4-yloxy)-phenyl]-amide(4-fluoro-phenyl)-amide A reactor was charged with 4-(6,7-dimethoxy-quinoline-4-yloxy)-phenylamine (35.7 kg, 1 equivalent), followed by THF (412.9 kg). To the reaction mixture was charged a solution of $K_2CO_3$ (48.3 kg) in water (169 kg). The acid chloride solution of described in the Alternative Preparation of 1-(4-Fluoro-phenylcarbamoyl)-cyclopropanecarbonyl chloride above was transferred to the reactor containing 4-(6,7-dimethoxy-quinoline-4-yloxy)-phenylamine while maintaining the temperature between 20 to 30° C. over a minimum of two hours. The reaction mixture was stirred at 20 to 25° C. for a minimum of three hours. The reaction temperature was then adjusted to 30 to 25° C., and the mixture was agitated. The agitation was stopped, and the phases of the mixture were allowed to separate. The lower aqueous phase was removed and discarded. To the remaining upper organic phase was added water (804 kg). The reaction was left stirring at 15 to 25° C. for a minimum of 16 hours.

The product precipitated. The product was filtered and washed with a mixture of water (179 kg) and THF (157.9 kg) in two portions. The crude product was dried under a vacuum for at least two hours. The dried product was then taken up in THF (285.1 kg). The resulting suspension was transferred to reaction vessel and agitated until the suspension became a clear (dissolved) solution, which required heating to 30 to 35° C. for approximately 30 minutes. Water (456 kg) was then added to the solution, as well as SDAG-1 ethanol (20 kg, ethanol denatured with methanol over two hours). The mixture was agitated at 15 to 25° C. for at least 16 hours. The product was filtered and washed with a mixture of water (143 kg and 126.7 kg THF (143 kg) in two portions. The product was dried at a maximum temperature set point of 40° C.

In an alternative procedure, the reaction temperature during acid chloride formation was adjusted to 10 to 15° C. The recrystallization temperature was changed from 15 to 25° C. to 45 to 50° C. for 1 hour and then cooled to 15 to 25° C. over 2 hours.

Preparation of cyclopropane-1,1-dicarboxylic acid [4-(6,7-dimethoxy-quinoline-4-yloxy)-phenyl]-amide(4-fluoro-phenyl)-amide, cabozantinib (S)-malate salt Cyclopropane-1,1-dicarboxylic acid [4-(6,7-dimethoxy-quinoline-4-yloxy)-phenyl]-amide(4-fluoro-phenyl)-amide (13.3 kg), L-malic acid (4.96 kg), methyl ethyl ketone (MEK; 188.6 kg) and water (37.3 kg) were charged to a reactor, and the mixture was heated to reflux (approximately 74° C.) for approximately 2 hours. The reactor temperature was reduced to 50 to 55° C., and the reactor contents were filtered. These sequential steps described above were repeated two more times starting with similar amounts of cyclopropane-1,1-dicarboxylic acid [4-(6,7-dimethoxy-quinoline-4-yloxy)-phenyl]-amide(4-fluoro-phenyl)-amide (13.3 kg), L-Malic acid (4.96 kg), MEK (198.6 kg), and water (37.2 kg). The combined filtrate was azeotropically dried at atmospheric pressure using MEK (1133.2 kg) (approximate residual volume 711 L; KF<0.5% w/w) at approximately 74° C. The temperature of the reactor contents was reduced to 20 to 25° C. and held for approximately 4 hours, resulting in solid precipitate which was filtered, washed with MEK (448 kg), and dried under vacuum at 50° C. to afford the title compound (45.5 kg).

Alternative Preparation of cyclopropane-1,1-dicarboxylic acid [4-(6,7-dimethoxy-quinoline-4-yloxy)-phenyl]-amide(4-fluoro-phenyl)-amide, (S) malate salt Cyclopropane-1,1-dicarboxylic acid [4-(6,7-dimethoxy-quinoline-4-yloxy)-phenyl]-amide(4-fluoro-phenyl)-amide (47.9 kg), L-malic acid (17.2 kg), methyl ethyl ketone (658.2 kg), and water (129.1 kg) were charged to a reactor, and the mixture was heated 50 to 55° C. for approximately 1 to 3 hours and then at 55 to 60° C. for an additional 4 to 5 hours. The mixture was clarified by filtration through a 1 µm cartridge. The reactor temperature was adjusted to 20 to 25° C. and vacuum distilled with a vacuum at 150 to 200 mm Hg with a maximum jacket temperature of 55° C. to the volume range of 558 to 731 L.

The vacuum distillation was performed two more times with the charge of 380 kg and 380.2 kg methyl ethyl ketone, respectively. After the third distillation, the volume of the batch was adjusted to 18 v/w of Cyclopropane-1,1-dicarboxylic acid [4-(6,7-dimethoxy-quinoline-4-yloxy)-phenyl]-amide(4-fluoro-phenyl)-amide by charging methyl ethyl ketone (159.9 kg) to give a total volume of 880 L. An additional vacuum distillation was carried out by adjusting methyl ethyl ketone (245.7 kg). The reaction mixture was left with moderate agitation at 20 to 25° C. for at least 24 hours. The product was filtered and washed with methyl ethyl ketone (415.1 kg) in three portions. The product was dried under a vacuum with the jacket temperature set point at 45° C.

In an alternative procedure, the order of addition was changes so that a solution of L-malic acid (17.7 kg) dissolved in water (129.9 kg) was added to Cyclopropane-1, 1-dicarboxylic acid [4-(6,7-dimethoxy-quinoline-4-yloxy)-phenyl]-amide(4-fluoro-phenyl)-amide (48.7 kg) in methyl ethyl ketone (673.3 kg).

The foregoing disclosure has been described in some detail by way of illustration and example for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The invention claimed is:

1. A method of treating endometrial cancer in a patient in need of such treatment, comprising administering to the patient once daily a pharmaceutical dosage comprising 60 mg of compound 1 as the L-malate salt:

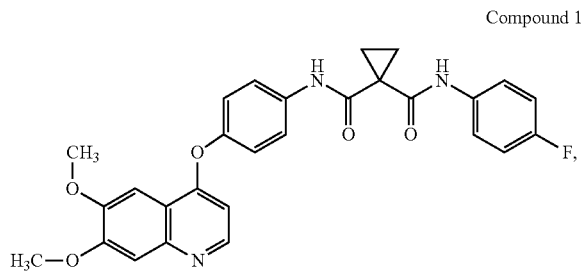 [SMILES: COc1cc2nccc(Oc3ccc(NC(=O)C4(C(=O)Nc5ccc(F)cc5)CC4)cc3)c2cc1OC]

Compound 1 wherein compound 1 L-malate salt is administered as a tablet comprising:

| Ingredient | (% w/w) |
|---|---|
| Compound 1 | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |

-continued

| Ingredient | (% w/w) |
| --- | --- |
| Croscarmellose Sodium | 3.00 |
| Magnesium Stearate | 0.75 |
| Total | 100.00. |

2. A method of treating endometrial cancer in a patient in need of such treatment, comprising administering to the patient once daily a pharmaceutical dosage comprising 40 mg of compound 1 as the L-malate salt:

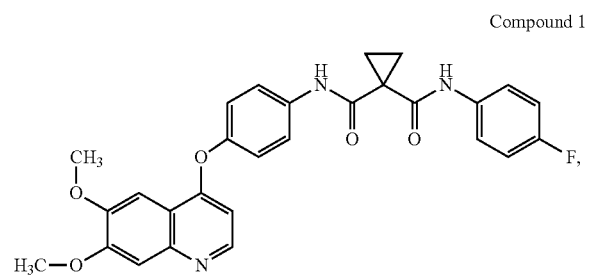 [SMILES: COc1cc2nccc(Oc3ccc(NC(=O)C4(C(=O)Nc5ccc(F)cc5)CC4)cc3)c2cc1OC]

Compound 1 wherein compound 1 L-malate salt is administered as a tablet comprising:

| Ingredient | (% w/w) |
| --- | --- |
| Compound 1 | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |

-continued

| Ingredient | (% w/w) |
| --- | --- |
| Magnesium Stearate | 0.75 |
| Total | 100.00. |

3. A method of treating endometrial cancer in a patient in need of such treatment, comprising administering to the patient once daily a pharmaceutical dosage comprising 20 mg of compound 1 as the L-malate salt:

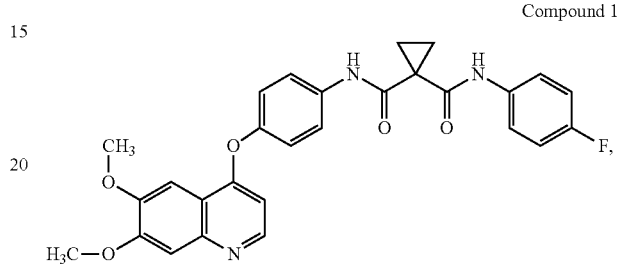

Compound 1 wherein compound 1 L-malate salt is administered as a tablet comprising:

| Ingredient | (% w/w) |
| --- | --- |
| Compound 1 | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00. |

* * * * *